(12) United States Patent
Mitchell et al.

(10) Patent No.: US 11,867,653 B2
(45) Date of Patent: Jan. 9, 2024

(54) SYSTEMS AND METHODS FOR MOUNTING BIOSENSORS USING A CONSUMABLE FLUID RESERVOIR

(71) Applicant: Adarza Biosystems, Inc., St. Louis, MO (US)

(72) Inventors: Jason Mitchell, St. Louis, MO (US); Bryan Witherbee, St. Louis, MO (US); Tracey Hodge, St. Louis, MO (US); Christopher Striemer, St. Louis, MO (US); David Merrigan, Limerick (IE); Martin Reddin, Limerick (IE); John-Paul Griffin, Limerick (IE); John Daly, Limerick (IE)

(73) Assignee: Monroe Biosensors, Inc., Penfield, NY (US)

(*) Notice: Subject to any disclaimer, the term of this patent is extended or adjusted under 35 U.S.C. 154(b) by 370 days.

(21) Appl. No.: 17/199,080

(22) Filed: Mar. 11, 2021

(65) Prior Publication Data
US 2021/0285908 A1    Sep. 16, 2021

Related U.S. Application Data

(60) Provisional application No. 62/988,335, filed on Mar. 11, 2020.

(51) Int. Cl.
*G01N 27/32* (2006.01)
*G01N 27/327* (2006.01)
*G01N 33/543* (2006.01)

(52) U.S. Cl.
CPC ..... *G01N 27/3272* (2013.01); *G01N 33/5438* (2013.01)

(58) Field of Classification Search
CPC ......... B01L 2200/026; B01L 2300/042; B01L 2300/043; B01L 2300/047; B01L 2300/0636; B01L 2300/0829; B01L 2300/0851; B01L 2300/087; B01L 3/502; B01L 3/5025; B01L 3/502707; G01N 27/3272; G01N 33/5438
See application file for complete search history.

(56) References Cited

U.S. PATENT DOCUMENTS

| | | | |
|---|---|---|---|
| 7,153,702 B2 * | 12/2006 | Lin ...................... | B01L 3/5085 436/805 |
| 8,652,320 B2 * | 2/2014 | Petyt ..................... | C12Q 1/006 204/403.01 |
| 9,535,028 B2 * | 1/2017 | Petyt ..................... | C12Q 1/006 |
| 2008/0087554 A1 | 4/2008 | Norris et al. | |
| 2010/0284863 A1 | 11/2010 | Downward et al. | |
| 2014/0326598 A1 | 11/2014 | Lee et al. | |
| 2016/0059201 A1 | 3/2016 | Ueda et al. | |
| 2016/0214113 A1 * | 7/2016 | Togawa ................... | B01L 9/52 |

FOREIGN PATENT DOCUMENTS

WO   2021/183798 A1   9/2021

OTHER PUBLICATIONS

International Search Report and Written Opinion relating to International Application No. PCT/US2021/021961, dated Jun. 22, 2021; 10 pgs.

* cited by examiner

*Primary Examiner* — Vinh P Nguyen
(74) *Attorney, Agent, or Firm* — POLSINELLI, PC

(57) ABSTRACT

A system and method for controlled fluid handling and processing of singulated biosensors. The system includes a consumable for mounting and protecting biosensors.

20 Claims, 9 Drawing Sheets

SYSTEMS AND METHODS FOR MOUNTING BIOSENSORS USING A CONSUMABLE FLUID RESERVOIR

RELATED APPLICATIONS

This application claims priority to U.S. Provisional Application No. 62/988,335, entitled "Consumable System for Molecule Detection Assays," filed Mar. 11, 2020. The contents of the aforementioned application are incorporated herein by reference in its entirety.

FIELD OF THE DISCLOSURE AND BACKGROUND

The disclosure describes systems and methods of mounting and protecting molecule detection assays, as well as providing enhanced fluid handling capabilities. There is a need to enable secure mounting of biosensors in a protective carrier that allows ease of use for an end user to introduce fluid onto the biosensor with a pipette or other fluid delivery mechanism, allow incubation time, and be introduced into an automation system in a singulated way which can subsequently remove the cap, wash, amplify, rinse, and dry the product, maintain a precise product level and orientation for optical measurement, and finally be collected in a waste bin.

BACKGROUND

Typical chip based biosensor technology may provide devices for mounting biosensors in protective carriers. However, these typical carriers do not allow biosensors to be individually accessed and handled by machine or human. Further, when arranged in a well plate, traditional carriers do not allow for a singulated system where individual biosensors may be easily mounted to or removed from a well plate while maintaining the integrity of the remaining biosensors. Additionally, typical carriers do not allow repeated access to the biosensors inside the carrier without destroying the integrity of the carrier. Typical carriers are also difficult to manufacture.

There is an unmet need for a scalable fluidic interface system that is easy to manufacture. What is also needed is a method of providing a scalable fluidic interface system with one or more biosensors. The system should have minimal parts, may be injection moldable, non-contaminating, and compatible with the back end of an automated manufacturing line where the biosensor is quickly mounted and packaged into the final product. The system should also be simple and easy to use.

SUMMARY

The present disclosure pertains to a novel system for mounting biosensors in a protective carrier. The system may comprise at least one consumable. The at least one consumable may comprise a cap seal. The cap seal may have a top surface and a bottom surface. The bottom surface of the cap seal may have adhesive properties. The consumable may also comprise a cap. The cap may have a bottom level, a middle level, and a top level. The cap may have only a bottom and a top level. The consumable may also comprise a biosensor. The consumable may include a bonding element. The bonding element may have a top surface and a bottom surface. One or both surfaces of the bonding element may be adhesive. The consumable may also have a base. The base may have a bottom level, a middle level, and a top level, or it may simply have a bottom level and a top level. The base and bonding element may have holes that allow the biosensor to be physically contacted from outside the carrier for alignment without having to be removed from the carrier. The top level of the cap has an internal volume, wherein the internal volume may be divided into a fluidic access port (inlet or outlet or vent) and a fluid reservoir (for sample addition or waste collection). The system may be used by placing the biosensor on the top surface of the bonding element. Next, the cap may be placed on the base. Next, a fluid may be added to the system by filling the fluid reservoir or inserting a fluid filled pipette into the fluidic access port. The fluid inside the system may be displaced by another fluid in subsequent assay steps. This solution exchange can be done as many times as required by the assay. Excess fluid from solution exchange may collect in the fluid reservoir and may be removed by a pipette or other fluidic removal device.

Other advantages of the disclosure will become apparent from the following description taken in connection with the accompanying drawings, wherein is set forth by way of illustration and example an embodiment of the present disclosure.

BRIEF DESCRIPTION OF THE DRAWINGS

In order to describe the manner in which the advantages and features of the present inventive concept can be obtained, reference is made to embodiments thereof which are illustrated in the appended drawings. Understanding that these drawings depict only exemplary embodiments of the present inventive concept and are not, therefore, to be considered to be limiting of its scope, the principles herein are described and explained with additional specificity and detail through the use of the accompanying drawings in which.

DETAILED DESCRIPTION

Figure 1:
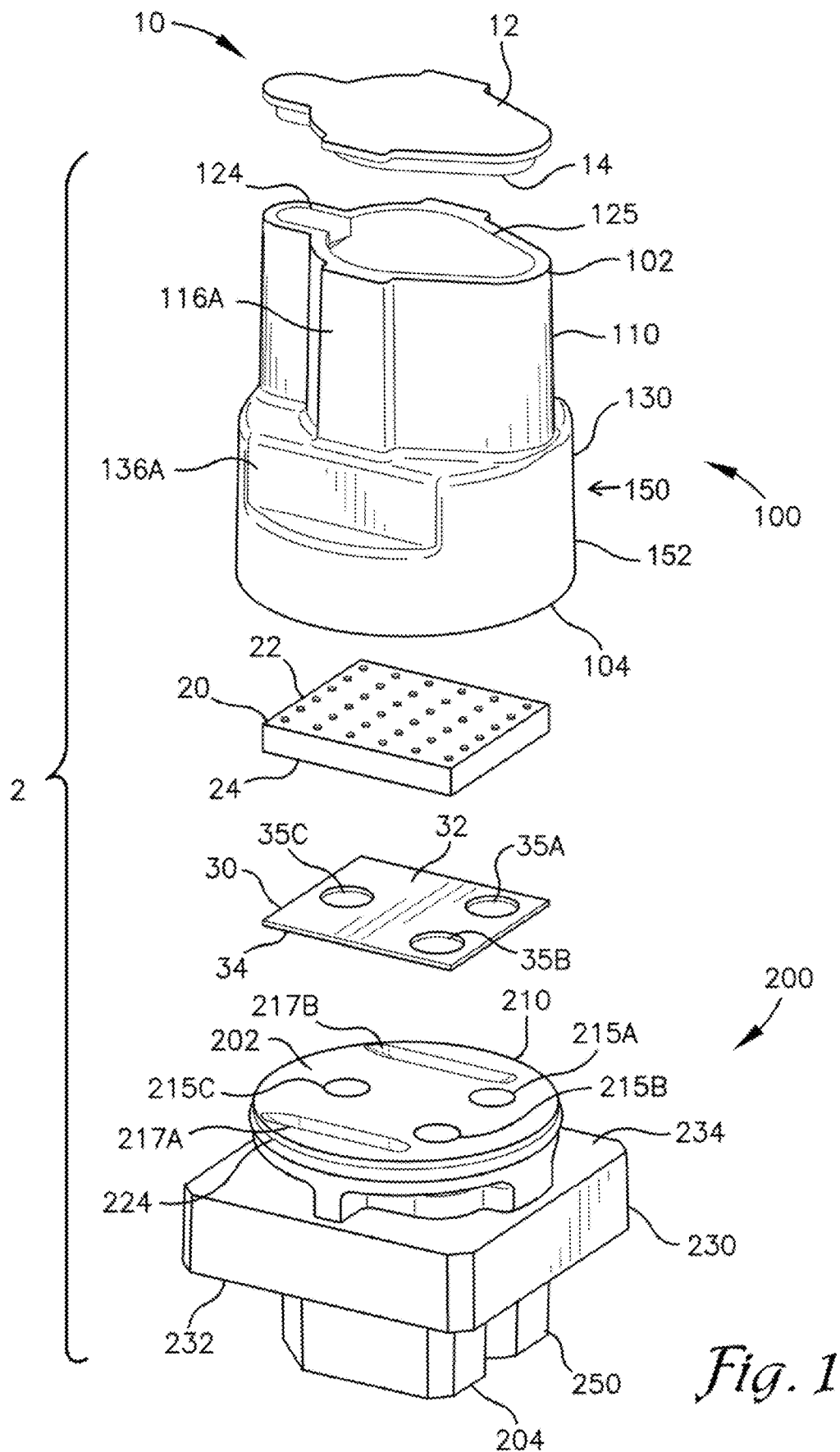
FIG. 1 illustrates an exploded view of the consumable system according to one embodiment.

As required, a detailed embodiment of the consumable system is disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The disclosure is for a consumable system 1 as shown in FIGS. 1-10 and a method of using consumable system 1 to run bioanalysis using various biosensors and other consumable products. Specifically, the disclosure is to a secure mount and protective carrier for biosensors that allows for interrogation and access to said biosensor for assay and measurement.

The consumable system 1 may comprise a consumable 2 for engaging a well plate 300. The consumable 2 may comprises a cap seal 10, a biosensor 20, a bonding element 30, a cap 100, a base 200, and a strip 350. The cap seal 10 may have a top surface 12 and a bottom surface 14 opposite the top surface 12. The biosensor 20 may be an Adarza® biosensor or any suitable biosensor. The well plate 300 may have a Society for Biomedical Sciences (SBS) footprint. One of skill in the art will appreciate that the well plate 300 may have any footprint or configuration known in the art. In some embodiments the consumable system 1 may include one or more strips 350 configured to securely receive and hold one or more consumables 2. In some embodiments, the strip 350 may be configured for the one or more consumables 2 to be individually placed or removed from the strip 350. Similarly, each strip 350 may be individually placed or removed from a well plate 300. Alternatively, the well plate 300 maybe be configured to securely receive and hold one or more consumables 2 directly without need for strip 350.

The cap 100 may have a top level 110, a bottom level 150 opposite the top level 110, and a middle level 130 between the top level and bottom level. The cap 100 has a top surface 102 which is also the top surface 102 of the top level 110. The cap 100 has a bottom surface 104 which is also the bottom surface 104 of the bottom level 150. As shown in FIG. 1 the middle level 130 is attached to the top level along the surface of the top level 110 that is opposite the top surface 102. The middle level 130 is also connected to the bottom level along the surface of the bottom level 150 that is opposite the bottom surface 104. The top level 110 has a sidewall 112. The sidewall 112 has an interior surface 113 and an outer surface 115. The interior surface 113 defines an internal cap volume. The internal cap volume may have a cap divider 122 that divides the internal cap volume into a fluidic access port 124 and a fluid reservoir 125. In some embodiments the fluidic access port 124 maybe be used as an inlet, outlet, or port for fluid exchange. In some embodiments the fluidic access port 124 may be shaped to allow for guiding and/or sealing a pipette or other fluidic interfacing device. In some embodiments, the internal cap volume may be divided into three, four, or more separate volumes. The fluid reservoir 125 has a bottom wall 127. The bottom wall 127 may have an aperture 128 which allows the fluid reservoir 125 to be in fluid communication with the incubation chamber 140 below the fluid reservoir. The fluidic access port 124 may be configured to accept multiple pipette tips. The cap 100 may be formed from a material such as plastic. One of skill in the art will appreciate that the cap 100 may be formed from other materials such as metals or polymers without departing from the disclosed subject matter or without sacrificing all of its material advantages.

The top level 110 of the cap 100 may include two top grip areas 116A-B. These top grip areas or sections 116 A-B may be configured for being handled and moved by a robot or instrument. In this regard, the top grip sections 116 A-B may have additional features that aid in grip. By way of non-limiting example, the top grip sections 116 A-B may include a rubber or other material or undercut feature that provides additional friction between the top grip sections 116 A-B and a robot or machine arm. In some embodiments, the top grip sections 116 A-B can be used to facilitate removal of the cap from the base.

Figure 7:
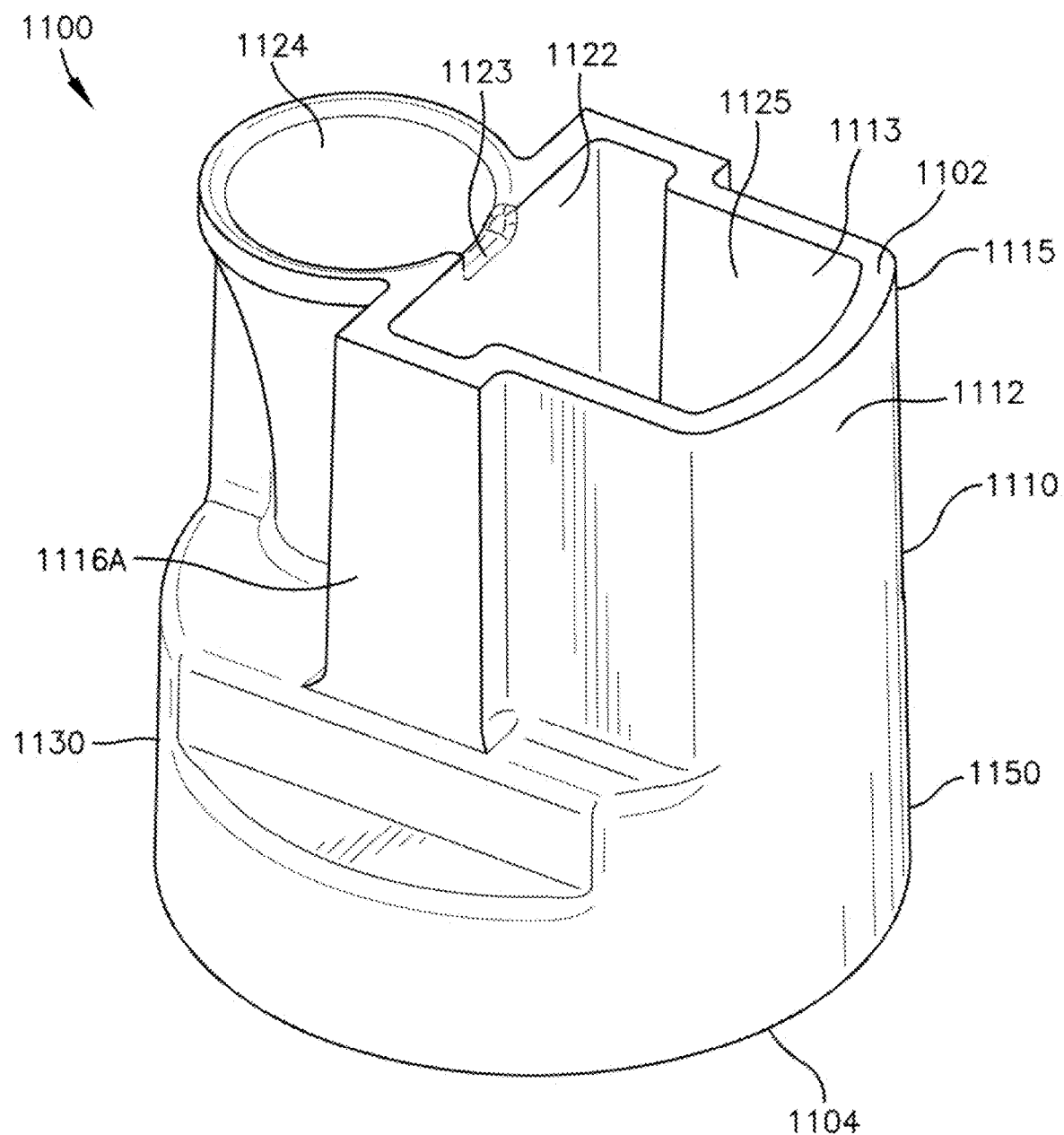
FIG. 7 illustrates a cap of the consumable systems according to one embodiment.
Figure 8:
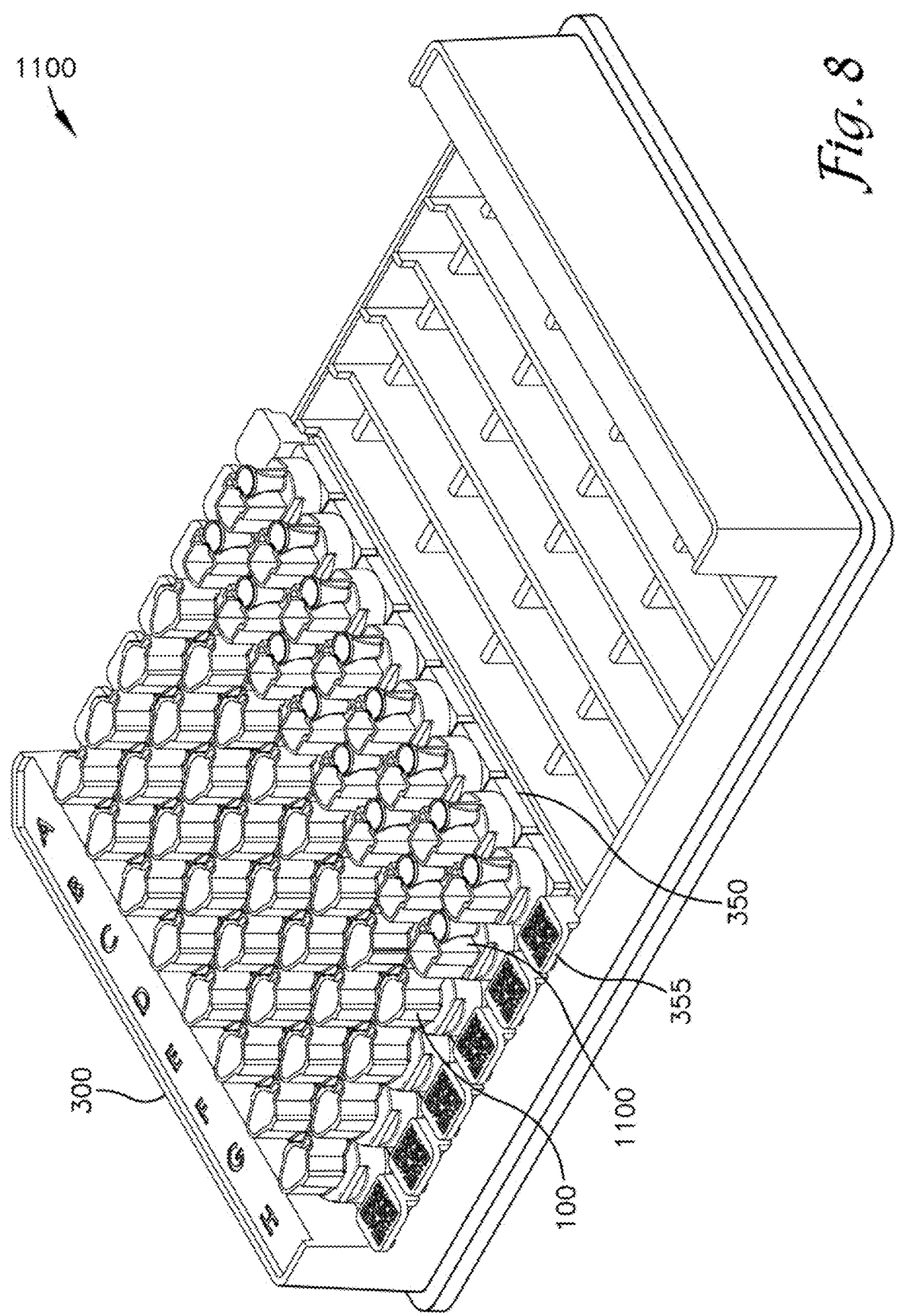
FIG. 8 illustrates an array of the consumable systems according to one embodiment.

Another embodiment of the cap 1100 is shown in FIGS. 7 and 8. This embodiment has a top level 1110, a bottom level 1150 opposite the top level 1110, and a middle level 1130 between the top level 1110 and bottom level 1130. The cap 1100 has atop surface 1102 which is also the top surface 1102 of the top level 1110. The cap 1100 has a bottom surface 1104 which is also the bottom surface 1104 of the bottom level 1150. As shown in FIG. 7 the middle level 1130 is attached to the top level along the surface of the top level 1110 that is opposite the top surface 1102. The middle level 1130 is also connected to the bottom level along the surface of the bottom level 1150 that is opposite the bottom surface 1104. The top level 1110 of the cap 1100 may include two top grip areas 1116A-B. These top grip areas 1116A-B may be configured for being handled and moved by a robot or instrument. The top level 1110 has a sidewall 1112. The sidewall 1112 has an interior surface 1113 and an outer surface 1115. The interior surface 1113 defines an internal cap volume.

In the embodiment shown in FIG. 7, the internal cap volume may have a cap divider 1122 that divides the internal cap volume into a fluidic access port 1124 and a fluid reservoir 1125. In this embodiment, the internal cap divider may have a cutout 1123 configured to allow overflow fluid to enter the fluidic access port 1124 from the fluid reservoir 1125 or to allow overflow fluid to enter the fluid reservoir 1125 from the fluidic access port 1124. In some embodiments the fluidic access port 1124 maybe be used as an inlet, outlet, or port for fluid exchange. As shown in FIG. 7, the fluidic access port 1124 of this embodiment may have a venturi or trumpet shape that provides for smooth guidance of a pipette tip into the port and will enable the formation a fluidic seal when using a broad range of commercial pipette tip designs. One of skill in the art will appreciate that the fluidic access port 1124, 124 may have any shape known in the art. One of skill in the art will also appreciate that the fluid reservoir 1125, 125 may have any shape known in the art.

Figure 2:
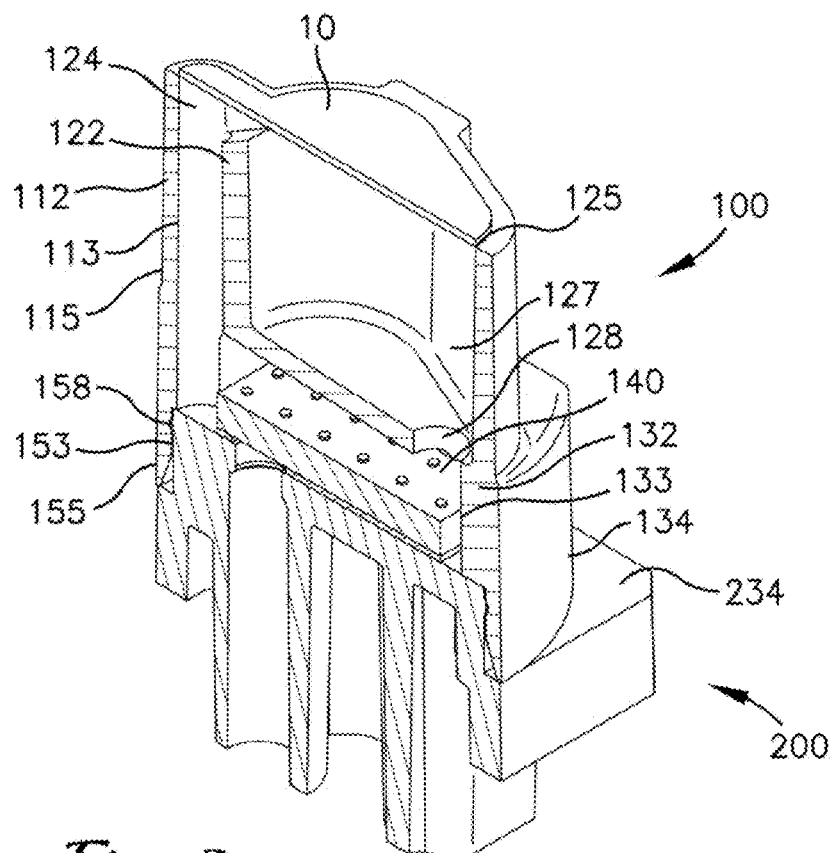
FIG. 2 illustrates a cross-sectional view of the consumable system according to one embodiment.

As shown in FIGS. 1 and 2, the middle level 130 has a sidewall 132. The sidewall 132 has an interior surface 133 and an outer surface 134. The interior surface 133 defines an incubation chamber 140. The incubation chamber 140 may be in fluid communication with the fluidic access port 124 and the fluid reservoir 125. The sidewall 132 is configured to reduce the total volume of the incubation chamber 140. In some embodiments, the incubation chambers volume may be in a range from less than 10 uL to greater than 50 uL. In other embodiments, the incubation chamber volume may be <10 uL, 10 uL to 25 uL, 25 uL to 50 uL or >50 uL. This reduced total volume provides the advantage of requiring a small sample fluid volume. The incubation chamber 140 may have a shape and dimensions to accommodate various shapes of biosensor 20. The incubation chamber 140 may preferably be cylindrical but other shapes for the incubation chamber 140 would be readily apparent to one of skill in the art, such as, for example, spherical, quadrilateral, or other shapes. In other embodiments, the shape of the incubation chamber 140 may depend on the geometry of the biosensor. As shown in FIG. 1 the middle level 130 may have two flat vertical wall areas 136A-B. These flat areas 136A-B reduce the required fluid volume in the incubation chamber 140, facilitate location alignment of the biosensor within the cap 100, enable the wall thickness to be maintained in the injection molding process, and may be configured to aid handling and moving by a robot or other suitable instrument. In this regard, the flat vertical wall sections 136 AB may have additional features that aid in gripping. By way of non-limiting example, the middle grip sections 136 AB may include a rubber or other material or undercut feature that provides additional friction between the middle grip sections 136 AB and a robot or machine arm.

Figure 9:
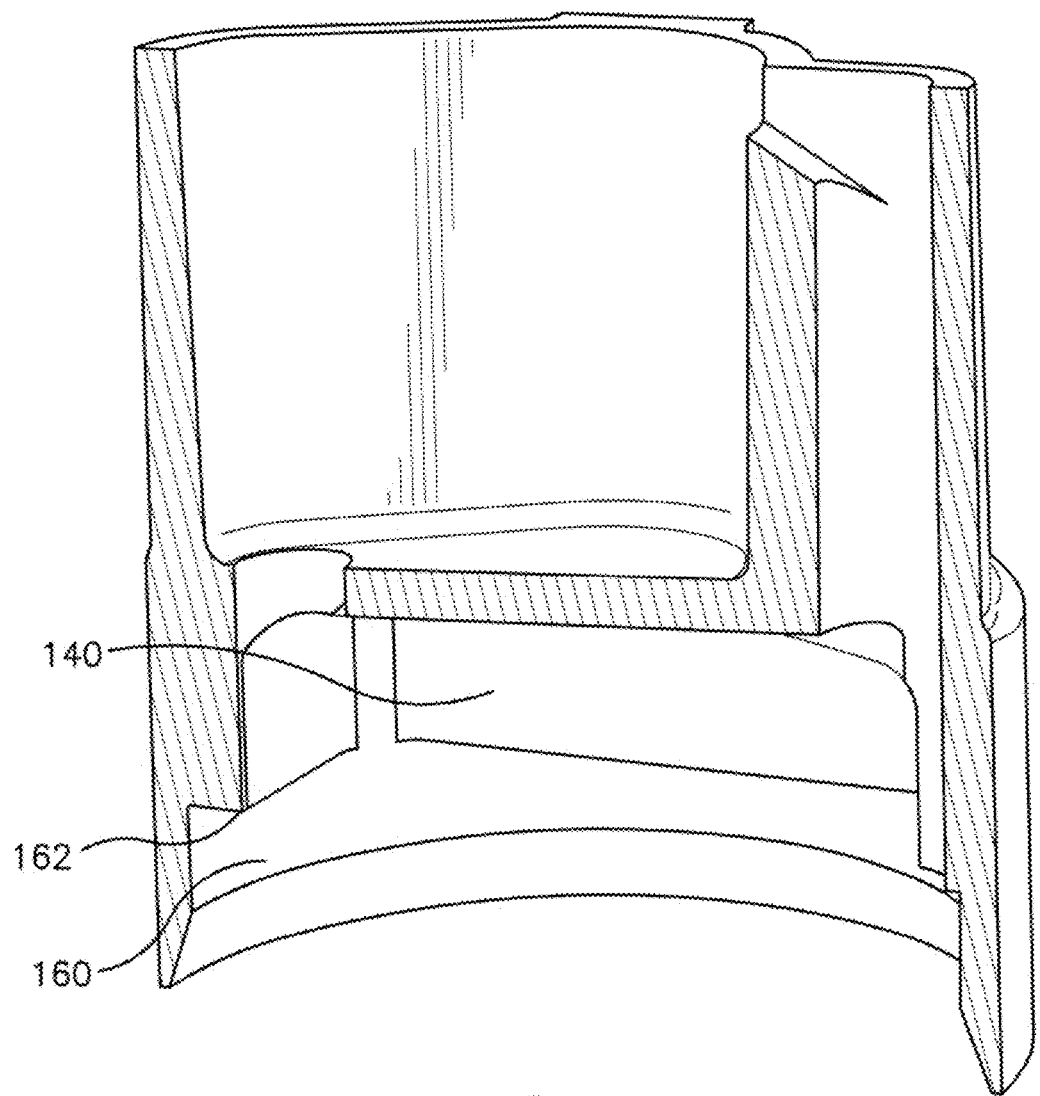
FIG. 9 illustrates a cross-sectional view of the consumable system according to one embodiment.

The bottom level 150 may be cylindrical. As shown in FIGS. 1 and 2 the bottom level 150 has a sidewall 152. The sidewall 152 has an interior surface 153 and an outer surface 155. The interior surface 153 defines an internal bottom cap volume 160. As shown in FIG. 9, the internal bottom cap volume 160 and the incubation chamber 140 may form a single space where the bottom cap volume 160 is closer to the bottom surface 104 than the incubation chamber 140. The bottom cap volume 160 may have a top wall 162 that partially separates the incubation chamber 140 from the bottom cap volume 160. The top wall 162 may be generally parallel to the top surface 102 of the top level 110 and also to the bottom surface 104 of the top level 110. Because the bottom cap volume 160 and the incubation chamber 140 are a continuous volume, the top wall 162 may have a gap such that the top level 162 is not a continuous surface. The internal bottom cap volume 160 is preferably configured to accept the base 200. In this regard, the interior surface 153 of the sidewall 152 engages a portion of the base 200. When the base 200 is accepted by the bottom cap volume 160, the top surface 202 of the base may abut the top wall 162 of the bottom cap volume.

The consumable 2 is configured to accept various biosensors. As shown in FIG. 1, the consumable 2 may be configured to accept an Adarza® biosensor. The biosensor 20 may have a top surface 22 and a bottom surface 24 opposite the top surface. The consumable system 1 allows individual biosensors 20 to be accessed while other biosensors are held in the strip 350. In this regard, individual biosensors may be directly dried, imaged or have fluid added. It should also be appreciated that two, three, four, or more, biosensors may be accessed. The biosensor 20 may be a silicon chip. One of skill in the art will appreciate that the biosensor may be any biosensor known in the art.

The base 200 may include top level 210, a bottom level 250 opposite the top level 210, and a middle level 230 between the top level 210 and bottom level 250. The base 200 has a bottom surface 204 which is also the bottom surface 204 of the bottom level 250. The base 200 has a top surface 202 opposite the bottom surface 204. As shown in FIG. 1, the middle level 230 is connected to the top level 210 along the surface of the top level 210 that is opposite the top surface 202. The middle level 230 is also connected to the bottom level along the surface of the bottom level 250 that is opposite the bottom surface 204. The bottom level 250 has a sidewall 252. The sidewall 252 has an interior surface 253 and an outer surface 255. As shown in FIGS. 1-3 and 6, the interior surface 253 may have one or more base dividers 262 that divide an internal area of the bottom level 150 of the base 200 into a plurality of base channels 261 A-C and a first and a second molding cavity 264 A-B. In some embodiments, the base 200 has more than three base channels 261. In other embodiments, the base 200 has less than three base channels 261. In some embodiments, the base 200 has more than two molding cavities 264. In other embodiments, the base 200 has less than two molding cavities 264. The base 200 may be formed by injection molding, extrusion or any other formation methods used in the art. In this regard, the molding cavities 264 AB aid in manufacturing the base by allowing a molding material to flow while minimizing warping or deformation during the cooling process. The base 200 may be formed from a material such as plastic. One of skill in the art will appreciate that the base 200 may be formed from other materials such as metals or polymers without departing from the disclosed subject matter or without sacrificing all of its material advantages.

Figure 10:
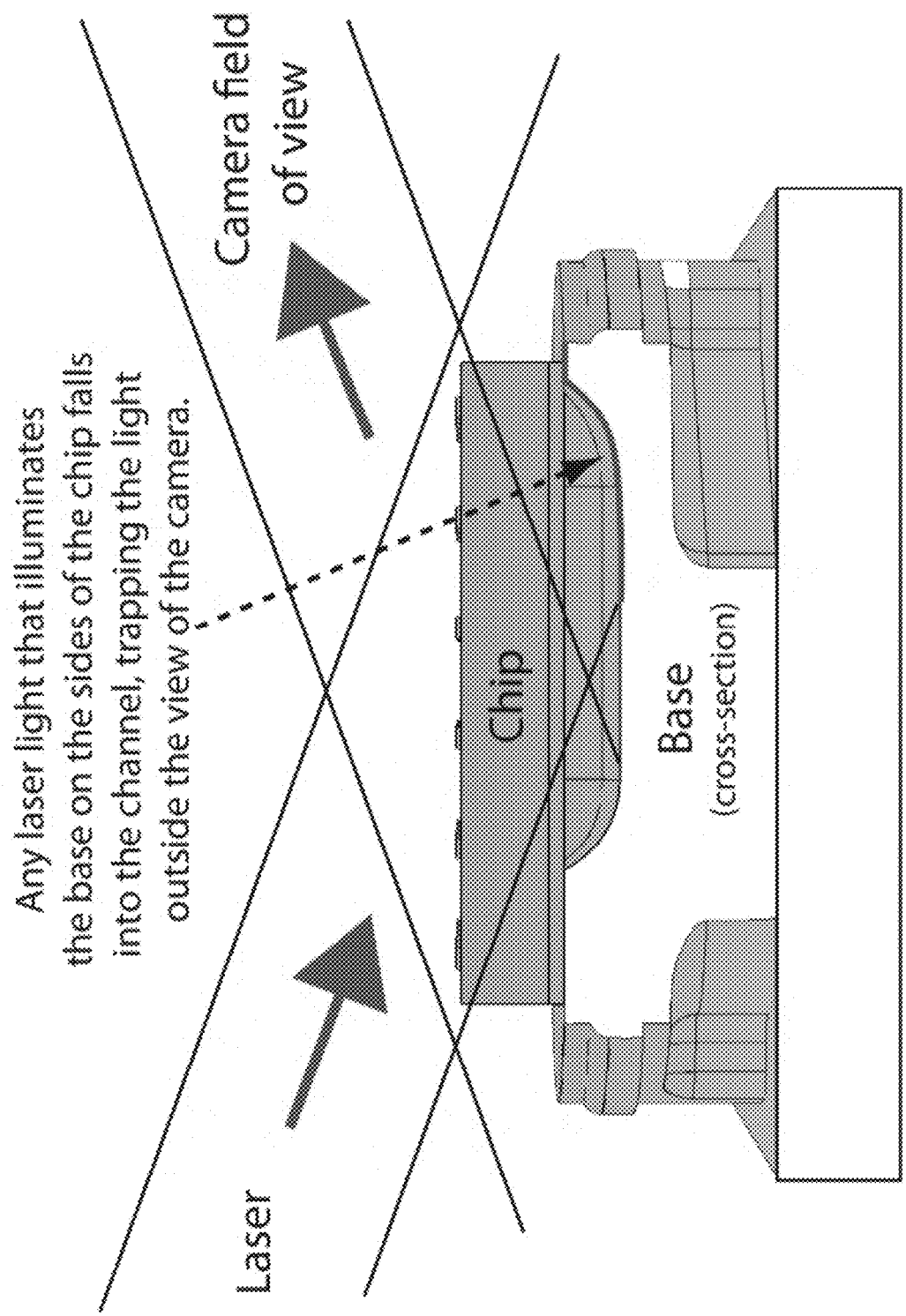
FIG. 10 illustrates a cross sectional view of a light trapping channel on the top surface of the base with visual representation of the light-trapping effect according to one embodiment.

As shown in FIG. 1, the top level 210 of the base 200 may have any shape known in the art. Preferably, the top level 210 of the base 200 is a circular shape which contributes to the lateral sealing stability of the fully assembled consumable 2. One of skill in the art will appreciate that the top level 210 of the base 200 may be any shape known in the art as long as the shape of the top level 210 contributes to the lateral sealing stability of the fully assemble consumable 2, for example, oval, rectangle, triangle, square, or any other shape known in the art. The top level 210 may include a plurality of top level apertures 215A-C. These top level apertures 215A-C may be in fluid communication with the base channels 261 A-C. The base channels 261 A-C are configured to allow a pin or other tool to physically access and contact the bottom surface 24 of the biosensor 20 or the bonding element 30 attached to the biosensor 20. In this regard, the base 200 is configured for precision leveling to the underside of the biosensor 20. In various aspects, this may be performed by positioning one or more pins or other rigid protrusions to contact the underside of the biosensor 20 as necessary to maintain a precise alignment of the device relative to a high-precision optical interrogation system. The middle level 230 of the base 200 may form a platform that has a top surface 234 and a bottom surface 232. The top level 210 of the base 200 may also include a first channel 217A and a second channel 217B. In some embodiments these channels may be described as troughs, trenches, or conduits. The first and second channels 217A-B may comprise an antireflective material or structure. In this regard, the first and second channels 217A-B may prevent light scattering and optical noise from entering an imaging system during interrogation of consumable 2. FIG. 10 illustrates one embodiment where excess light that would otherwise produce imaging glare off the top surface 202, instead falls into such channel 217A-BB and out of the region viewable by the camera. Without such structures, excess light could overwhelm the imaging system of the camera and make imaging of the biosensor challenging. The first and second channels 217A-B may also provide fluidic pathways to assist in liquid removal during a pressurized airflow drying process. The top level 210 of the base 200 may have a lip 224 surrounding the top level 210. The lip 224 may act as an additional seal by engaging the interior surface 153 which prevents leaking from the cap 100 to base 200 connection when the consumable 2 is completely assembled. In some embodiments, the base 200 may comprise a top and a bottom level without a middle level.

As shown in FIG. 1, the cap 100 of the consumable 2 may be sealed by placing the cap seal 10 on top of the top surface 102 of the cap such that the bottom surface 14 of the cap seal 10 is removably attached to the top surface 102 of the cap. The cap seal 10 and the top surface 102 of the cap 100 are attached to prevent evaporation during incubation or hold times. Some embodiments of the consumable 2 may not include a cap seal 10.

The consumable may include a bonding element 30 of rectangular or other geometry required to affix the biosensor 20 to base 200. Some embodiments may minimize the area of the bonding element in the form of thin rings around the apertures 35A-C. Some embodiments may connect aforementioned thin rings with thin strips of bonding material to maintain a monolithic bonding element. The bonding element 30 may also provide a fluidic seal to the top level apertures 215A-C allowing a biosensor 20 to be mechanically referenced with high precision. The bonding element 30 may be a double sided tape or other pressure sensitive adhesive material known in the art. The bonding element 30 may have a top surface 32 and a bottom surface 34 opposite the top surface 32. Each surface 32, 34 of the bonding element 30 may have adhesive properties allowing the bonding element to be attached to the base and a suitable biosensor 20. The bonding element 30 may have a plurality of bonding element apertures 35A-C. These bonding element apertures 35 A-C are configured to align with the top level apertures 215A-C of the base. In this regard, the bonding element 30 may be placed and adhered to the top level 210 of the base 200 so that each of the top level apertures 215A-C align with the bonding element apertures 35A-C. When the bonding element is placed on top of the top level 210 of the base 200, the bottom surface 34 of the bonding element 30 is in contact with the top surface 202 of the base. The top surface 32 of the bonding element 30 may be attached to the bottom surface 24 of a biosensor 20 in order to firmly hold the biosensor in place. The bonding element 30 may also form a fluidic seal between the incubation chamber 140 and channels 261 A-C. Some embodiments may use glue, epoxy, cement or other liquid or gel-like materials as the bonding element. Some embodiments may use mechanical tolerance or flexible elements to hold the biosensor mechanically to the base 200.

Figure 3:
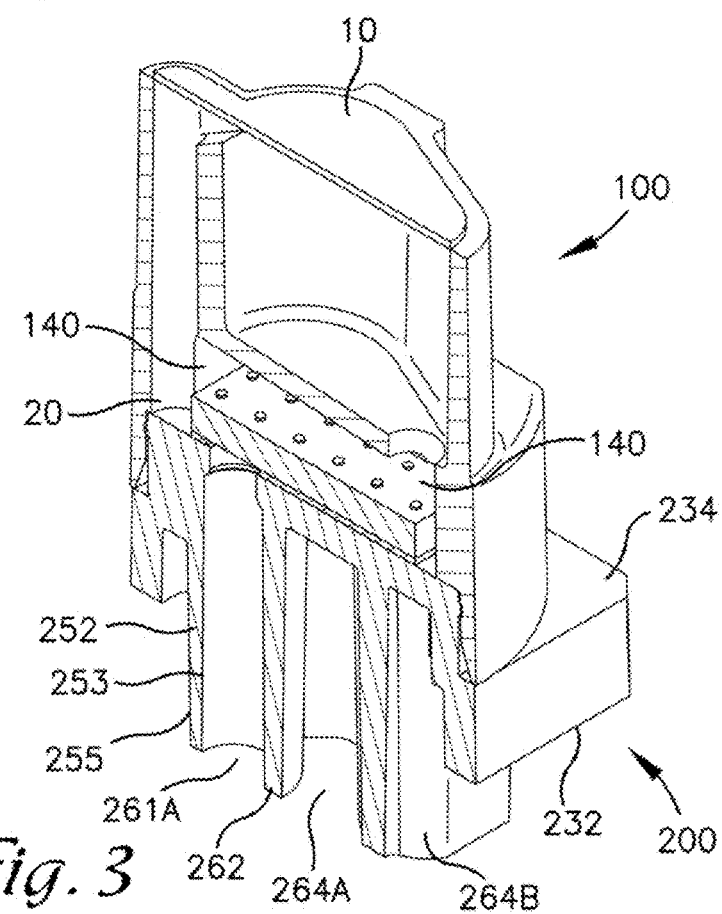
FIG. 3 illustrates a cross-sectional view of the consumable system according to one embodiment.
Figure 4:
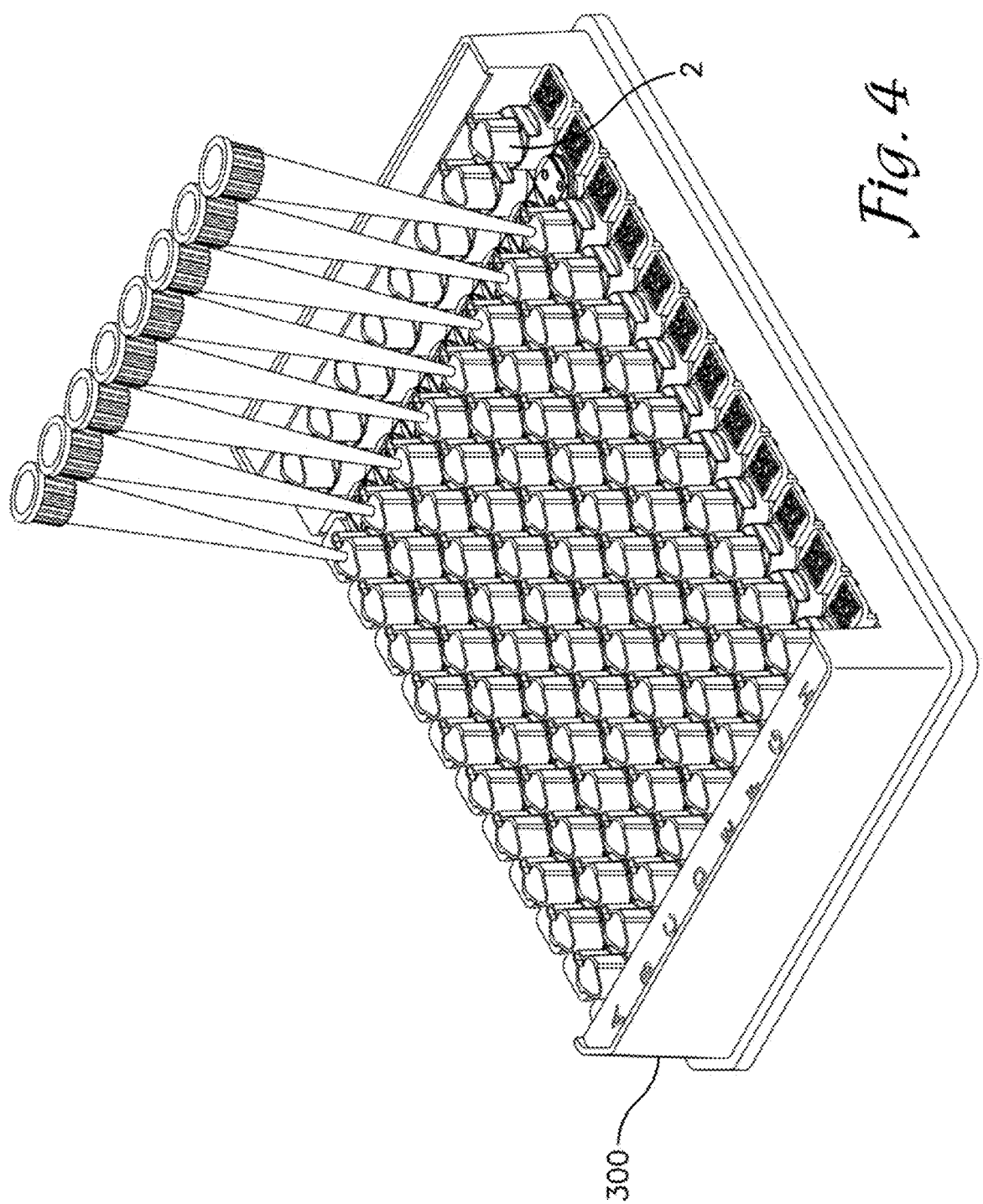
FIG. 4 illustrates an array of the consumable systems according to one embodiment.

Once the biosensor 20 is attached to the top surface 202 of the base 200 via the bonding element 30, the cap 100 may be placed over the base 200. The cap 100 may be placed over the base 200 such that the bottom surface 104 of the cap 100 is touching or nearly touching the top surface 234 of the middle level 230 of the base 200. As shown in FIGS. 2-3, when assembled, the interior surface 153 of the cap 100 forms a seal with the lip 224 of the base. This seal prevents leakage of fluids between the base 200 and the cap 100. In some embodiments the inner diameter of interior 153 may be less than the outer diameter of lip 224 to provide additional sealing force.

As shown in FIGS. 2-3, the consumable 2 is assembled by mounting the biosensor 20 on the top surface 202 of the base 200 via the bonding element 30. Further, the bottom level 150 of the cap 100 is placed or slid over the top level 210 of the base 200 so the bottom surface 104 of the cap 100 abuts the top surface 234 of the middle level 230. Because the consumable 2 may be used with biosensors 20 that may require direct drying and imaging, of the biosensor 20, the cap 100 may be removable from the base 200. In some embodiments, the cap 100, the biosensor 20, or both, may be removeable. In some embodiments the cap 100 and the base 200 may be permanently attached to one another. When the cap 100, biosensor 20, bonding element 30, and base 200 are assembled, the incubation chamber 140 is defined by the bottom wall 127 of the fluid reservoir 125, the sidewall 132 of the middle level 130 of the cap 100, and the top surface 202 of the base 200. As discussed above, the internal cap volume 160 is configured to accept the base 200. In this regard, the incubation chamber 140 is a space configured to contain the biosensor 20 mounted on the top surface 202 of the base 200 via the bonding element 30. A fluid may be introduced into the fluid reservoir 125 or the fluidic access port 124. The fluid may comprise an appropriate biosample. One of skill in the art will appreciate that the biosample may comprise blood, urine, other bodily fluids, exudates, secretions, tissue samples, serum, and/or other bio-molecular material known in the art. Because the fluid reservoir 125 and the incubation chamber 140 are in fluid communication via the aperture 128, fluid may enter the incubation chamber 140, where the biosensor is located. Due to surface tension, wetting properties of the cap 100 and biosensor 20, and gravity, fluid is then pulled across the biosensor 20. Without the cap seal 10 in place, air is allowed to escape from the fluidic access port 124 and the fluid reservoir 125. Additional fluids may be added to the fluidic access port 124 or the fluid reservoir 125. By way of non-limiting example, the additional fluid may include multiple reagents. When additional fluids are added to the fluidic access port 124, the additional fluids may enter the incubation chamber 140. In turn, the pressure from the additional fluid in the incubation chamber 140 may force fluid out of the incubation chamber 140 and into the fluid reservoir 125. The configuration of the incubation chamber 140 provides a chamber that requires minimal fluid sample volume.

Figure 5:
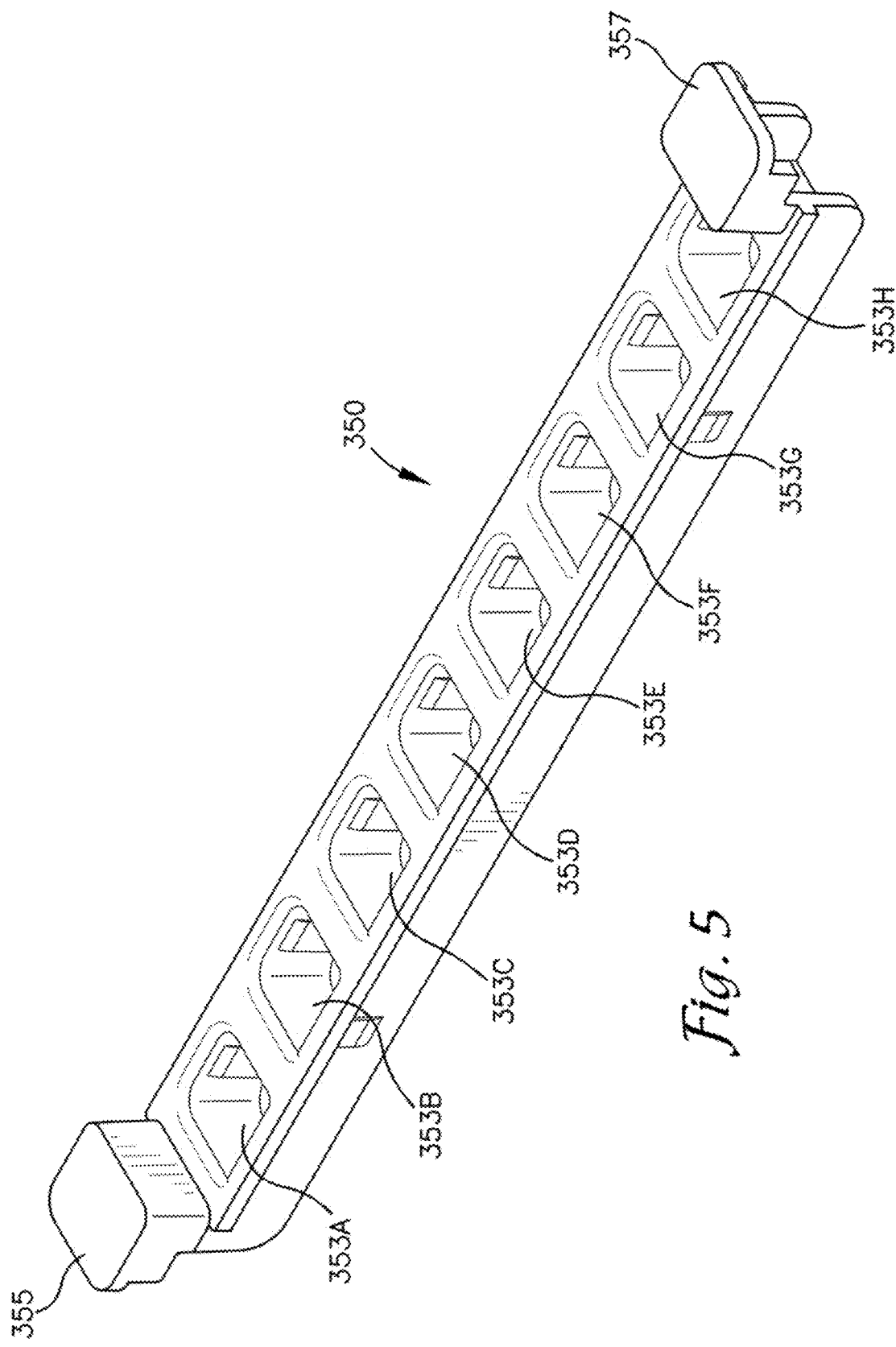
FIG. 5 illustrates a holder strip for the consumable systems according to one embodiment.
Figure 6:
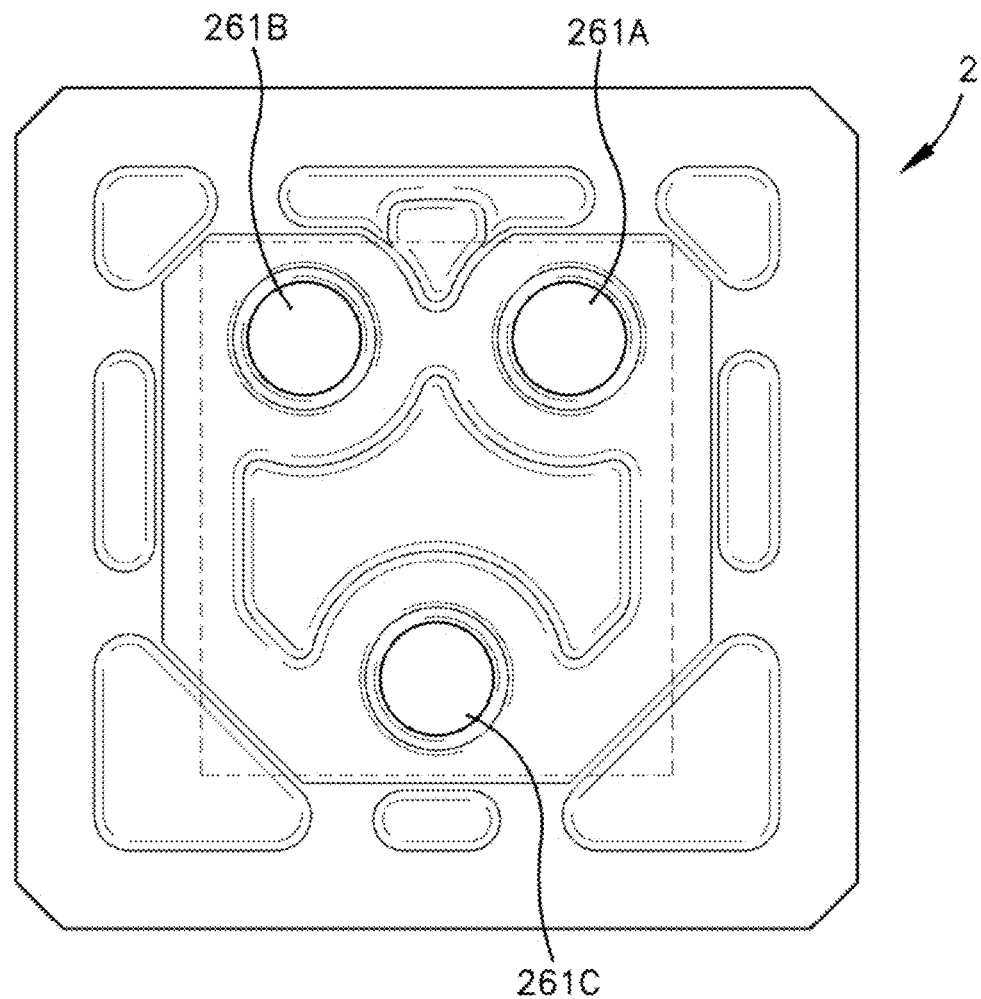
FIG. 6 illustrates a bottom view of the consumable system according to one embodiment.

After the consumable 1 has been assembled, the cap seal may be placed on the top surface 12 of the consumable 2 in order to seal the consumable 2. The consumable 2 may be placed in a well of the well plate 300. The consumable 2 may also be placed in a consumable aperture 353 A-H of a strip 350 which is then inserted into well plate 300. As shown in FIG. 5. The strip 350 may have a plurality of strip apertures 353 A-H configured to accept and securely hold one or more bases 200. One of skill in the art will appreciate that the strip 350 may have more or less than eight strip apertures 353 A-H, without departing from the disclosed subject matter or without sacrificing all of its material advantages. In this regard, the strip 350 may be configured to be accepted by a well plate 300 in any direction known in the art, including longitudinal and lateral. The strip 350 may also have a first end 355 opposite a second end 357. One or both the first end 355 and the second end 357 may be configured to rest on a well plate 300 in a manner that allows the strip 350 to be removed from the well plate 300. One or both the first end 355 and the second end 357 may also be configured carry identification that can be read visually, or using systems and device capable of reading bar codes, QR codes, RFID tags, NFC or other identification systems known in the art. Because the consumable system 1 may be used with automated robots, the indicia may include instructions and identification for automation. Strip 350 may also be configured with mechanical keying features that ensure proper insertion orientation into strip 350 or well plate 300.

The base 200 of one or more consumables 2 may be placed in the strip apertures 353 A-H. The strip 350 may be placed in the well plate 300. The bonding element 30 may be attached to the top surface 202 of the base 200. In some embodiments, the bonding element 30 is attached to the bottom surface 24 of the biosensor. When the well plate 300 is fully loaded with strips 350 which are fully loaded with bonding element 30 bearing bases 200, the system is ready to accept biosensors. In this regard, the configuration is biosensor manufacturing ready. One of skill in the art will appreciate that the well plate 300 may be biosensor manufacturing ready when less than fully loaded with bases 30 or strips 350. The biosensor 20 may be placed and adhered to the top surface 202 of the base 200. The cap 100 may be slid over the base 200. A sample containing fluid may be introduced into the cap 100 via the fluid reservoir 125 and/or fluidic access port 124. The cap may be sealed by placing the cap seal 10 on the top surface 102 of the cap 100. Each consumable 2 may be added to or removed from the strip 350, alone or simultaneously with other consumables 2.

Each strip 350 may be added to or removed from the well plate 300, alone or simultaneously with other strips 350. In some embodiments, each strip 350 may be joined together by placing the strips in the well plate 300. Strips 350 that are joined together in the well plate 300 may also be separated before or after the well plate 300 has been processed. In this regard, the consumable system 1 may present a monolithic well plate 300 that resembles a typical SBS microplate to a human user, while the consumable system 1 may be individually singulated in an automated machine. In some embodiments, the consumable 2, the strips 350 and the well plate 300 are assembled using automated assembly techniques known in the art. Because the components of the consumable system are disposable, the components may be discarded after use. One of skill in the art will appreciate that each component of the consumable system 1 may be manually moved or manipulated. One of skill in the art will also appreciate that each component of the consumable system 1 may be moved or manipulated using any robot known in the art. In this regard, each step of assembling the consumable system 1 may be automated. Similarly, an automated bioassay system may utilize the consumable system 1.

It is should be understood that consumable system 1 is designed to meet a series of requirements throughout its usage life from biosensor manufacturing to packaging to assay to final processing in a compatible instrument. In manufacturing, a plate 300 loaded with strips 350 and manufacturing ready bases serves as a carrier for convenient placement of up to 96 completed biosensors 20. It also serves as a precise rectangular array for simultaneous application of up to 96 caps and is fully compatible with manufacturing automation. Completely assembled plates 300 also serve as robust and protective packaging for the assay product system for stable storage and shipping. The consumable system is also compatible with all manual and automated processes required for running the assay by the end user, including the addition of biological samples and subsequent reagents, various methods of agitation including shaking, rocking, vibration or other agitations methods known in the art, and incubation at temperatures ranging from 4 C to 40 C. Final processing may include insertion and handling by an automated processing and reading instrument, and consumable 2 singulation, inversion, cap removal, biosensor 20 washing, application of amplifying reagents to biosensor 20, biosensor 20 rinsing, biosensor 20 drying, and optical interrogation of biosensor 20. It is understood by those of skill in the area that these compatibilities and processes can occur in any combination and temporal order.

The ease of use of the consumable system may be enhanced by using materials of various colors and levels of the transparency to make the fine functional features more visible to the user. Some color and transparency combinations may make the fluidic access port and fluid reservoir more obvious for manual pipetting operations using of single channel or multichannel pipettors. Transparency or translucency may also allow for visual confirmation of fluid entry into the consumable system and reduce error rates in assay performance.

In other embodiments of consumable 2 may allow for multiple biosensors 20 to be applied to a single base 200. Each biosensor 20 could have its own cap 100 and cap seal 10. Adding additional biosensors 20 to the base 200 may have throughput advantage for the relevant assay and processing of biosensor 20.

It should be understood from the foregoing that, while particular embodiments have been illustrated and described, various modifications can be made thereto without departing from the spirit and scope of the disclosure as will be apparent to those skilled in the art. Such changes and modifications are within the scope and teachings of this disclosure as defined in the claims appended hereto.

The invention claimed is:

1. A system for mounting biosensors in a protective carrier:
the system comprising at least one consumable, the at least one consumable comprising:
a cap;
a biosensor;
a bonding element;
a base; and,
a strip configured to hold at least a portion of the at least one consumable, and,
a well plate configured to hold at least one strip.

2. The system of claim 1, wherein the base comprises at least two levels, and wherein a first level of the base is configured to mount a biosensor.

3. The system of claim 1, wherein the cap defines at least one internal volume; the at least one internal volume defined by a cap sidewall and the base.

4. The system of claim 3, wherein the at least one internal volume has a divider, wherein the divider divides the internal volume into a fluidic access port and a fluid reservoir.

5. The system of claim 3, wherein the at least one internal volume is in fluid communication with an incubation chamber.

6. The system of claim 1, wherein a bottom level of the base is configured to be accepted by a strip in a friction fit.

7. The system of claim 1, wherein the strip is configured to be accepted by a well plate in a friction fit.

8. The system of claim 1, wherein the biosensor is an arrayed imaging reflectometry (AIR) sensor chip for small or large molecule detection.

9. The system of claim 1, wherein a portion of a cap sidewall is configured to be engaged by a robotic arm.

10. The system of claim 1, wherein the bonding element is configured to bond the biosensor to the top surface to the base.

11. The system of claim 1, wherein the cap is configured to fit on top of the base to form a biosensor incubation volume between the base and the cap.

12. The system of claim 11, wherein the biosensor incubation volume can be filled with a fluid.

13. The system of claim 1, wherein the base further comprises at least one channel configured to allow a tool to access a bottom surface of the biosensor.

14. The system of claim 1, wherein the consumable further comprises a cap seal.

15. The system of claim 1, wherein a top portion of the consumable is further configured to trap light, scatter light, or reduce optical noise.

16. A system for mounting biosensors in a protective carrier, the system comprising at least one consumable, the at least one consumable comprising:
a cap having a bottom level, a middle level, and a top level;
a biosensor;
a bonding element;
a base having a bottom level and a top level;
wherein the top level of the cap has an internal volume defined by a cap sidewall and the base, wherein the internal volume is divided into a fluidic access port and a fluid reservoir;
wherein the middle level of the cap has an incubation chamber configured to house the biosensor;

wherein the bottom level of the cap has a bottom cap volume configured to accept the top level of the base;

a strip configured to hold at least one consumable; and a well plate configured to hold at least one strip.

17. A method of mounting a biosensor in at least one consumable, the method comprising:
   a. providing the at least one consumable, the at least one consumable comprising:
      a cap having a bottom level, a middle level, and a top level;
      a biosensor;
      a bonding element;
      a base having a bottom level and a top level;
      wherein the top level of the cap has an internal volume defined by a cap sidewall and the base, wherein the internal volume is divided into a fluidic access port and a fluid reservoir;
      wherein the middle level of the cap has an incubation chamber configured to house the biosensor;
      wherein the bottom level of the cap has a bottom cap volume configured to accept the top level of the base; and,
   b. providing at least one strip configured to hold at least one consumable;
   c. providing a well plate configured to hold at least one strip;
   d. placing the biosensor on the top surface of the bonding element;
   e. placing the cap on the base;
   f. placing the base in the at least one strip; and
   g. adding fluid to the fluidic access port or the fluid reservoir.

18. The method of claim 17, wherein the well plate is placed in placed in a bioassay machine.

19. The method of claim 17, wherein the consumable is placed in the well plate without the strip.

20. The method of claim 17, wherein the bonding element is placed on the base before the biosensor is placed on the base.

* * * * *